United States Patent
Bencini (10) Patent No.: US 8,945,117 B2
(45) Date of Patent: Feb. 3, 2015

(54) INSULATED ABLATION CATHETER DEVICES AND METHODS OF USE

(75) Inventor: Robert F. Bencini, Sunnyvale, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1036 days.

(21) Appl. No.: 12/702,396

(22) Filed: Feb. 9, 2010

(65) Prior Publication Data
US 2010/0204691 A1 Aug. 12, 2010

Related U.S. Application Data (60) Provisional application No. 61/151,709, filed on Feb. 11, 2009.

(51) Int. Cl.
*A61B 18/14* (2006.01)
*A61B 17/00* (2006.01)
*A61B 18/00* (2006.01)

(52) U.S. Cl.
CPC ... *A61B 18/1492* (2013.01); *A61B 2017/00084* (2013.01); *A61B 2018/00011* (2013.01); *A61B 2018/00101* (2013.01); *A61B 2018/00214* (2013.01); *A61B 2018/00791* (2013.01)
USPC .......................................................... 606/41

(58) Field of Classification Search
CPC ................. A61B 18/1492; A61B 2018/00101; A61B 2018/00577; A61B 2018/00714; A61B 2018/00791
USPC ................................................ 606/27, 34, 41
See application file for complete search history.

(56) References Cited

U.S. PATENT DOCUMENTS

| | | | |
|---|---|---|---|
| 4,945,912 A | | 8/1990 | Langberg |
| 5,151,100 A | * | 9/1992 | Abele et al. .................. 606/28 |
| 5,230,349 A | | 7/1993 | Langberg |
| 5,398,683 A | | 3/1995 | Edwards et al. |
| 5,545,161 A | | 8/1996 | Imran |
| 5,643,197 A | * | 7/1997 | Brucker et al. ............... 604/20 |
| 5,676,693 A | | 10/1997 | LaFontaine |
| 5,836,875 A | | 11/1998 | Webster, Jr. |
| 5,913,854 A | * | 6/1999 | Maguire et al. .............. 606/41 |
| 5,919,188 A | | 7/1999 | Shearon et al. |
| 6,002,968 A | * | 12/1999 | Edwards .................... 607/101 |
| 6,006,755 A | * | 12/1999 | Edwards .................... 128/898 |
| 6,030,379 A | | 2/2000 | Panescu et al. |
| 6,162,184 A | | 12/2000 | Swanson et al. |
| 6,171,275 B1 | | 1/2001 | Webster, Jr. |

(Continued)

FOREIGN PATENT DOCUMENTS

WO WO 01/41664 6/2001
WO WO 2004/093703 11/2004

*Primary Examiner* — Michael Peffley
*Assistant Examiner* — Daniel Fowler
(74) *Attorney, Agent, or Firm* — Seager, Tufte & Wickhem, LLC (57) ABSTRACT

Disclosed herein is a catheter device sized and shaped for vascular access that has an elongate body extending between a proximal end and a distal end. Further, the elongate body has at least one inner lumen configured to receive a fluid. The catheter also has an ablation electrode configured to provide ablative energy, wherein the electrode is located distally along the elongate body and includes a passageway fluidly connected to the lumen of the elongate body. Also, the catheter has a sensor configured to provide a signal representative of temperature, and an insulating chamber extending at least partially about the ablation electrode and configured to at least partially insulate the sensor.

22 Claims, 6 Drawing Sheets

(56) References Cited

U.S. PATENT DOCUMENTS

| | | |
|---|---|---|
| 6,241,724 B1 | 6/2001 | Fleischman et al. |
| 6,258,087 B1 * | 7/2001 | Edwards et al. ............ 606/41 |
| 6,500,174 B1 * | 12/2002 | Maguire et al. ............ 606/41 |
| 6,547,788 B1 * | 4/2003 | Maguire et al. ............ 606/41 |
| 6,569,162 B2 * | 5/2003 | He ............ 606/41 |
| 6,589,238 B2 * | 7/2003 | Edwards et al. ............ 606/41 |
| 6,663,622 B1 | 12/2003 | Foley et al. |
| 6,972,016 B2 * | 12/2005 | Hill et al. ............ 606/41 |
| 7,125,409 B2 | 10/2006 | Truckai et al. |
| 7,507,237 B2 | 3/2009 | Geistert |
| 2003/0004506 A1 | 1/2003 | Messing |
| 2005/0288667 A1 * | 12/2005 | Thompson et al. ............ 606/41 |
| 2006/0271032 A1 | 11/2006 | Chin et al. |
| 2007/0270791 A1 | 11/2007 | Wang et al. |

\* cited by examiner

INSULATED ABLATION CATHETER DEVICES AND METHODS OF USE

The present disclosure claims priority under 35 U.S.C. §119(e) to U.S. Provisional Patent Application No. 61/151,709, which was filed on Feb. 11, 2009, which is also hereby incorporated by reference in its entirety.

FIELD

The present disclosure relates to the field of ablation and, more particularly, to insulated ablation catheter devices and methods of use.

BACKGROUND

Atrial fibrillation is a heart condition whereby abnormal electrical signals cause irregular heart contractions. One treatment for this condition includes open heart surgery and creating several lesions in the endocardium of the atria. These lesions can function to block aberrant electrical impulses, permitting an impulse originating from the sinus node to properly regulate heart contraction. However, because open heart surgery is highly invasive and requires a lengthy patient recovery period, alternate methods for making lesions are required. One alternative procedure uses ablation catheters.

Typically, an ablation catheter is advanced into the heart via the patient's blood vessels. When the catheter's electrodes are placed in the desired position within the heart chamber, radio frequency ("RF") energy is supplied to the catheter. Such RF energy ablates the tissue surrounding the ablation electrode, thereby creating a lesion in the endocardium.

Traditional ablation catheters included an elongated shaft with an ablation electrode mounted at the distal end of the shaft. Point or linear lesions could be formed with these catheters by manipulating the placement of the distal tip. However, creating suitable lesions using these catheters can be difficult because the tip electrode may overheat during ablation. Newer catheter designs mitigated these disadvantages by cooling the tip electrode during use, thereby minimizing the risk of overheating.

However cooled ablation catheters are limited in their ability to accurately determine the temperature of tissue surrounding the tip electrode. Temperature sensors of such catheters typically sense the temperature of the cooling fluid rather than tissue temperature. Accurate tissue temperature readings are desirable as they can provide a useful indication of tissue ablation. Accordingly, the present disclosure provides devices and methods for accurately determining tissue temperature that overcomes some of the disadvantages of current ablation technologies.

SUMMARY

Described herein are medical treatments for delivering ablative energy to target tissue while providing improved devices and methods for determining tissue temperature. In one aspect, an ablation catheter having an ablative electrode and an insulating chamber is disclosed. The catheter can include a pathway for providing cooling fluid to the ablative tip. Within the tip, cooling fluid can circulate in an open loop or closed loop configuration.

In one embodiment, a catheter device can be sized and shaped for vascular access. The catheter can include an elongate body extending between a proximal end and a distal end. Further, the elongate body can include at least one inner lumen configured to receive a fluid. The catheter can also include an ablation electrode configured to provide ablative energy, wherein the electrode can be located distally along the elongate body and can include a passageway fluidly connected to the lumen of the elongate body. The catheter can also include a sensor configured to provide a signal representative of temperature. In addition, the catheter can include an insulating chamber extending at least partially about the ablation electrode and configured to at least partially insulate the sensor from the ablation electrode.

Another aspect of the current disclosure is directed to a method for ablating tissue. The method includes the steps of providing an ablation electrode, wherein the ablation electrode can include a passageway fluidly connected to a lumen of an elongate body of a catheter device, an insulating chamber extending at least partially about the ablation electrode, and a temperature sensor at least partially insulated from the ablation electrode. The method can further include delivering fluid to the lumen to cool the ablation electrode, and delivering ablative energy to the ablation electrode.

Another aspect of the current disclosure is directed to an ablation electrode device configured to provide ablative energy to cardiac tissue. The electrode device can include a proximal section configured for attachment to an elongate body of a catheter device. The electrode device can further include a passageway configured to connect to a lumen of the elongate body, wherein the passageway can be configured to receive a fluid. Also included can be a sensor configured to provide a signal representative of a temperature of a region external to the ablation electrode. In addition, the electrode device can include an insulating chamber extending at least partially about the ablation electrode and configured to at least partially insulate the sensor.

Yet another aspect of the current disclosure is directed to a method of manufacturing an ablation electrode. The method can include providing a passageway configured to connect to a lumen of an elongate body of a catheter device, wherein the passageway can be configured to receive a fluid. The method can further include providing an insulating chamber extending at least partially about the ablation electrode. Also, the method can include attaching a sensor to the insulating chamber, wherein the sensor can be configured to provide a signal representative of a temperature of a region external to the ablation electrode.

It is to be understood that both the foregoing general description and the following detailed description are exemplary and are not restrictive of the present disclosure, as claimed. In addition, structures and features described with respect to one embodiment can similarly be applied to other embodiments.

BRIEF DESCRIPTION OF THE DRAWINGS

The accompanying drawings, which are incorporated in and constitute a part of this specification, provide illustrative embodiments of the present disclosure and, together with the description, serve to explain the disclosure's principles.

DETAILED DESCRIPTION

Disclosed herein are ablation catheters and methods of use. In general, the catheters include a flow path that provides cooling to a distal section of the catheter. The catheter can include an ablation electrode having irrigation apertures for delivery of a cooling fluid to the environment surrounding the electrode or to the surface of the electrode. In addition, the electrode can include an insulating chamber to at least partially thermally insulate a temperature sensor from other heat sources, such as, for example, the electrode or cooling fluid. The insulating chamber can improve the accuracy of sensing the temperature of the tissue or fluid surrounding the electrode.

Figure 1:
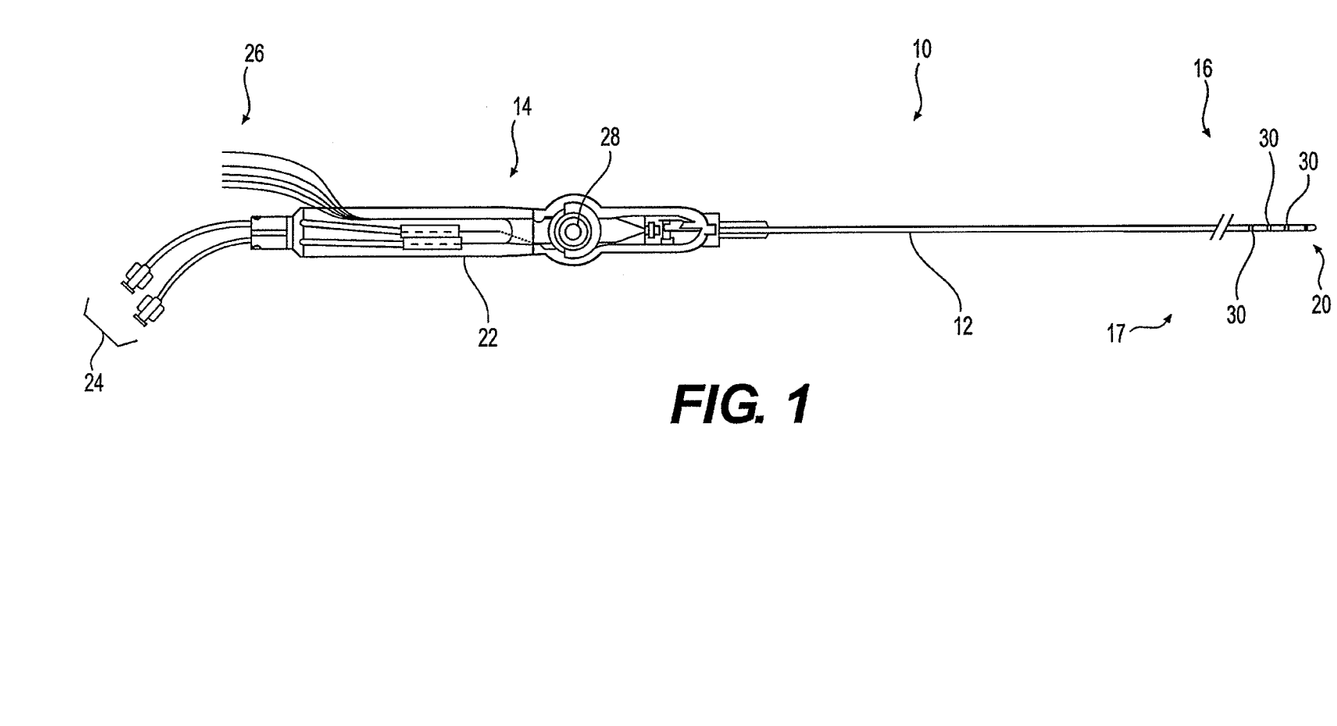
FIG. 1 illustrates a partially transparent view of one exemplary embodiment of an ablation catheter.

FIG. 1 provides a cut-away view of one exemplary embodiment of an ablation catheter device 10 for use with the electrode structure described herein. Catheter device 10 can include an elongate body 12 extending between a proximal section 14 and a distal section 16. Distal section 16 includes an ablation electrode 20, configured to deliver ablative energy to tissue as discussed in detail below.

In one aspect, proximal portion 14 of device 10 can include a handle 22 configured for use by a user. To permit operation of device 10, handle 22 can incorporate a variety of features to facilitate control of the catheter or the ablation process. For example, handle 22 can be configured to connect catheter device 10 to a source of fluid, a source of ablative energy, a temperature display, sensors, or control software or hardware. In particular, handle 22 can provide a source of cooling fluid for electrode 20 via one or more ports 24, configured to receive or expel fluid. In addition, device 10 can include mating elements 26 for receiving or transmitting energy to electrodes located distally along elongate body 12, such as, for example, electrode 20. One skilled in the art will appreciate that a variety of catheter handle configurations are contemplated depending on the features of the elongate body 12, ablation electrode 20, or the intended use of catheter device 10.

In some embodiments, catheter device 10 can be articulating. For example, catheter device 10 can include an articulating section 17, located distally along elongate body 12. Specifically, distal section 16 can be deflected or bent in one or more directions. Articulation can provide one or more degrees of freedom and permit up/down or left/right movement of elongate body 12. One skilled in the art will understand that catheter 10 can include a variety of features associated with conventional articulating catheter devices.

Articulating section 17 can be controlled via a proximally located control mechanism 28. Control mechanism 28 can be mounted on handle 22 and can direct movement of distal section 16 of elongate body 12. Such movement of elongate body 12 can facilitate insertion of catheter device 10 through a body lumen, such as, for example, vasculature. Control mechanism 28 can also manipulate distal section 16 to place electrode 20 at a target tissue location.

Elongate body 12 can be defined by a flexible cylindrical structure extending between handle 22 and distal section 16. In one embodiment, body 12 can house at least one lumen configured to receive a fluid. Such fluid can be transferred to electrode 20 for cooling purposes. In addition, body 12 can house electrical conductors, such as, for example, wires for transmitting sensed signals or ablation energy. Also, articulation mechanisms, such as, for example, control wires, can extend within body 12 to articulation section 17 to permit movement of catheter device 10. One skilled in the art will appreciate that body 12 can include a variety of structures shaped and sized to pass through a body cavity, such as, for example, a vascular lumen.

Where catheter device 10 includes articulating section 17, control wires (e.g., push/pull wires) can be configured to mate with distal section 16 of elongate body 12. For example, a reinforcing or anchor member (not shown) could be positioned within distal section 16. One or more control wires could mate with the reinforcing member to anchor the distal end of the control wire. However, such wires can alternatively, or additionally, be fixed at a more proximal location of device 10.

Distal section 16 of catheter device 10 can include at least one electrode for delivering ablation energy, sensing physiological signals, or functioning as a return electrode. In one aspect, one or more ring electrodes 30 can be located distally along elongate body 12. Ring electrodes 30 can, for example, permit sensing or mapping of cardiac signals. FIG. 1 illustrates three ring electrodes 30 within distal section 16 and positioned proximally from electrode 20. Various ring electrodes 30 or electrode 20 can be used to sense physiological signals. Mapping is usually accomplished using a pair of electrodes, including, for example, electrode 20.

In addition to sensing, distal section 16 of device 10 can be configured to deliver ablation energy using bipolar or monopolar signals. For example, radio frequency (RF), microwave, or other ablative energy can be delivered via one or more electrodes, such as, for example, ablation electrode 20. One or more ring electrodes 30, or a separate ground pad, can function as a return electrode.

FIGS. 2 to 5 illustrate various exemplary embodiments of ablation electrode 20. In one aspect, electrode 20 is configured to deliver RF energy to target tissue. To reduce coagulum formation, electrode 20 can include a flow path, indicated by arrow 21, for regulating the temperature of electrode 20. A build up of biological materials on the outer surface of electrode 20 or in the area surrounding electrode 20 can result in less effective energy transfer to the tissue. This effect can be seen as a rise in impedance and a corresponding increase in tissue heating or charring immediately adjacent to ablation electrode 20. Cooling of electrode 20 can permit more efficient energy transfer to tissue and allow larger lesion sizes. For example, cooling fluid moving through electrode 20 can absorb heat to reduce the electrode's temperature.

In some embodiments, a flow path can direct fluid through electrode 20 to the outer surface of electrode 20. The fluid can function as a conduit to transmit RF energy to tissue. Also, movement of fluid around electrode 20 while device 10 is in contact with tissue can reduce impedance rise as energy is delivered to the tissue. In some situations, the movement of the fluid can sweep biological material, such as, for example, blood and tissue, away from electrode 20 to reduce the build-up of embolic material.

Catheter device 10 also includes at least one insulating chamber configured to at least partially reduce heat transfer associated with conventional ablation catheters. Previously, temperature readings from the distal tip of ablation catheters could be affected by the other heat sources. Specifically, the temperature of the cooling fluid could modify the temperature sensed at a distal tip. Also, ablation electrodes can increase in temperature during an ablative procedure, again reducing the temperature measurement's accuracy.

In some embodiments, an insulating chamber 62 is configured to at least partially insulate a temperature sensor 46 from distal section 16 of catheter device 10. Insulating chamber 62 can contain air, other fluid, or a solid material. Such insulating substances are designed to reduce energy flow between temperature sensor 46 and other components of distal section 16. Temperature sensor 46 may then be configured to accurately sense the temperature of the environment or region surrounding distal section 16. Such temperature information can provide a better indication of tissue ablation.

Figure 2:
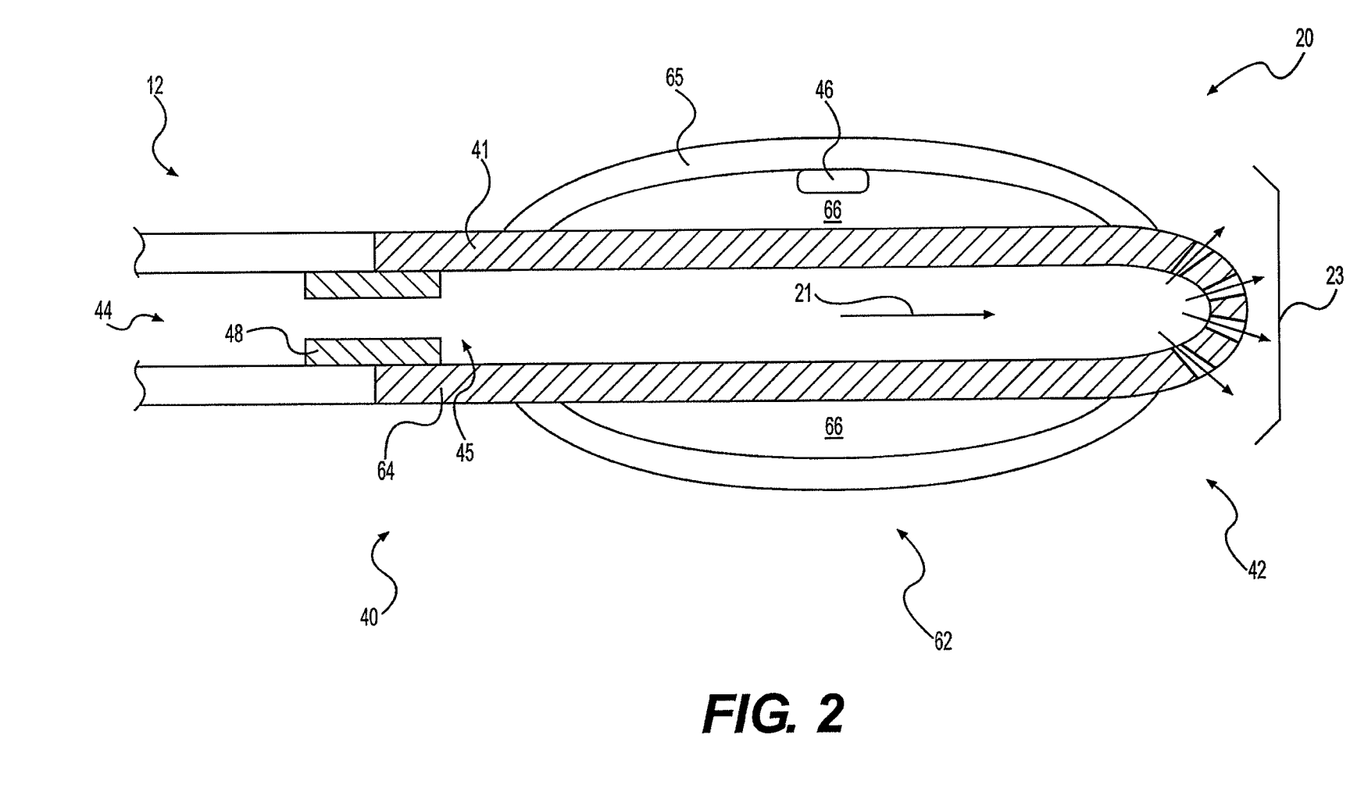
FIG. 2 illustrates a cross-sectional view of one embodiment of an ablation electrode described herein.

FIG. 2 illustrates one embodiment of electrode 20 having a proximal end 40 and a distal end 42, wherein proximal end 40 can be configured to mate with elongate body 12. In one embodiment, a connecting member 48 can be configured to connect electrode 20 and elongate body 12. For example, connecting member 48 could be a generally cylindrical structure configured to mate with an inner surface of body 12 and electrode 20. Alternatively, electrode 20 and body 12 could mate via an overlapping connection (not shown), whereby a portion of electrode 20 or body 12 could be positioned within or about a portion of the other structure. One skilled in the art will appreciate that a variety of mating mechanisms could be used, including frictional, mechanical, or adhesive engagements. In other embodiments, a sheath could extend about part of elongate body 12 or electrode 20.

In one embodiment, electrode 20 includes a body 41 configured to provide ablation energy to tissue. Body 41 can be constructed of a single unibody structure or of multiple segments of similar or different materials. Irrespective of its construction, body 41 can be formed of a variety of electrically and/or thermally conductive materials including, for example, platinum, iridium, stainless steel, gold, plated brass, and combinations thereof. In another aspect, body 41 could be an electrically conductive material, but not necessarily a thermally conductive material.

Electrode 20 can be configured to operate with various lumens, wires, or control mechanisms. In particular, proximal end 40 of electrode 20 can be configured to mate with various lumens, wires, or control mechanisms extending through body 12. For example, a passageway 45 within electrode 20 could be configured to receive fluid. In some embodiments, passageway 45 can be in fluid communication with a lumen 44 associated with elongate body 12. Fluid may flow into catheter device 10 via ports 24 (as shown in FIG. 1), through lumen 44 and into passageway 45. In other embodiments, one or more lumens may be fluidly connected with one or more passageways in electrode 20.

In some embodiments, one or more apertures 23 may be configured to direct a fluid from passageway 45 to a region surrounding electrode 20. As illustrated in FIG. 2, four apertures 23 are shown although a different number of apertures 23 may also be used. As discussed below with respect to FIG. 3, electrode 20 may include no apertures.

In some embodiments, catheter device 10 can include insulating chamber 62 located distally along device 10. In particular, insulating chamber 62 can be positioned proximal to at least a portion of electrode 20 or adjacent to distal end 42 of electrode 20. Further, insulating chamber 62 can at least partially extend, or extend substantially, about electrode 20. By at least partially surrounding an outer surface of electrode 20, insulating chamber 62 can provide at least some insulation from energy originating from distal section 16. For example, insulating chamber 62 can function to reduce heat transfer to a distally located temperature sensor 46, such as, for example, a thermocouple or thermistor. In some embodiments, sensor 46 may be located within insulating chamber 62.

Insulating chamber 62 can be configured to form various shapes. For example, insulating chamber 62 could be a generally cylindrical shape, extending in a longitudinal direction parallel to a longitudinal axis of electrode 20. Such a curvilinear form may also include linear or curvilinear sections. In particular, insulating chamber 62 could be a "peanut" shape, including generally bulbous distal and proximal sections and a smaller section between. Insulating chamber 62 could also be generally pear shaped or generally spherical.

In one aspect, insulating chamber 62 can include a sidewall 65. Sidewall 65 could be constructed of any suitable material, such as, for example, an alloy, a polymer, a ceramic, or combinations thereof. Sidewall 65 may be mated with a sidewall 64 of electrode body 41 via welding, heat sealing, friction fit, or other methods known in the art. Sidewall 65 may also be at least partially insulated from sidewall 64 to at least partially reduce heat transfer from sidewall 64 to sidewall 65. For example, sidewall 65 may be bonded to sidewall 64 using an insulative glue or other suitable adhesive. Also, sidewall 64 and/or sidewall 65 may be formed from or bonded with, in part or in whole, an insulative material.

Insulating chamber 62 can include an enclosed volume 66 that provides at least a partial insulative function. In particular, volume 66 can partially insulate sensor 46 from one or more heat sources. In some embodiments, volume 66 may be defined by a region enclosed by sidewalls 64 and 65. Also, volume 66 could be at least partially filled with various fluids or solids. For example, volume 66 could be filled with air, nitrogen, water, saline solution, foam, polymer, or ceramic material. Such substances may have low thermal and/or electrical conductivity.

Figure 3:
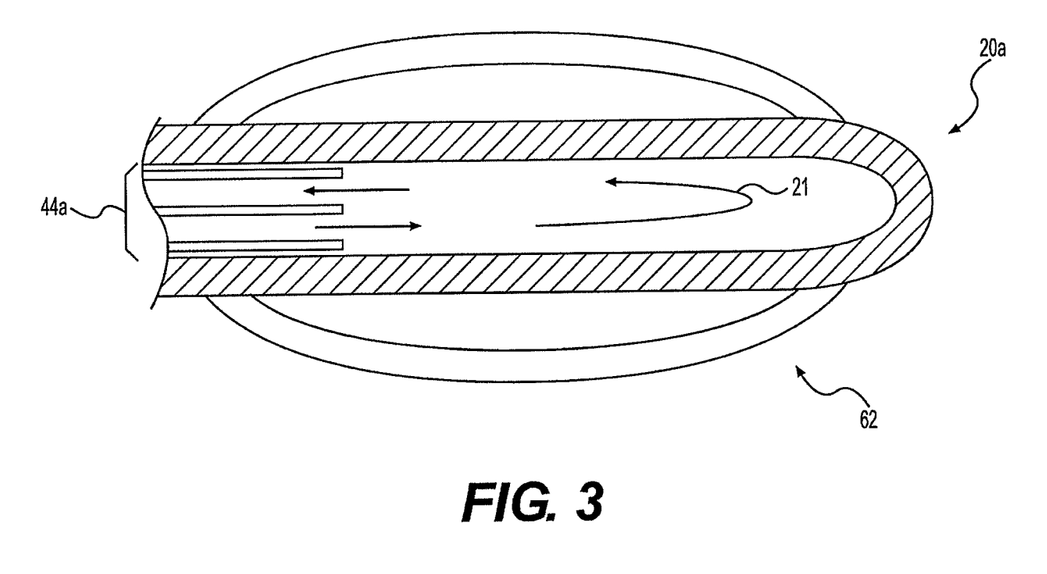
FIG. 3 illustrates a cross-sectional view of another embodiment of an ablation electrode.

As illustrated in FIG. 3, electrode 20a may operate with a closed loop fluid circulation system. Specifically, fluid flow 21 may enter and exit electrode 20a via two or more lumens 44a. While electrode 20a contains no apertures, fluid can be expelled from electrode 20a via a lumen 44a configured to receive fluid flow 21 and transfer fluid away from electrode 20a.

Figure 4:
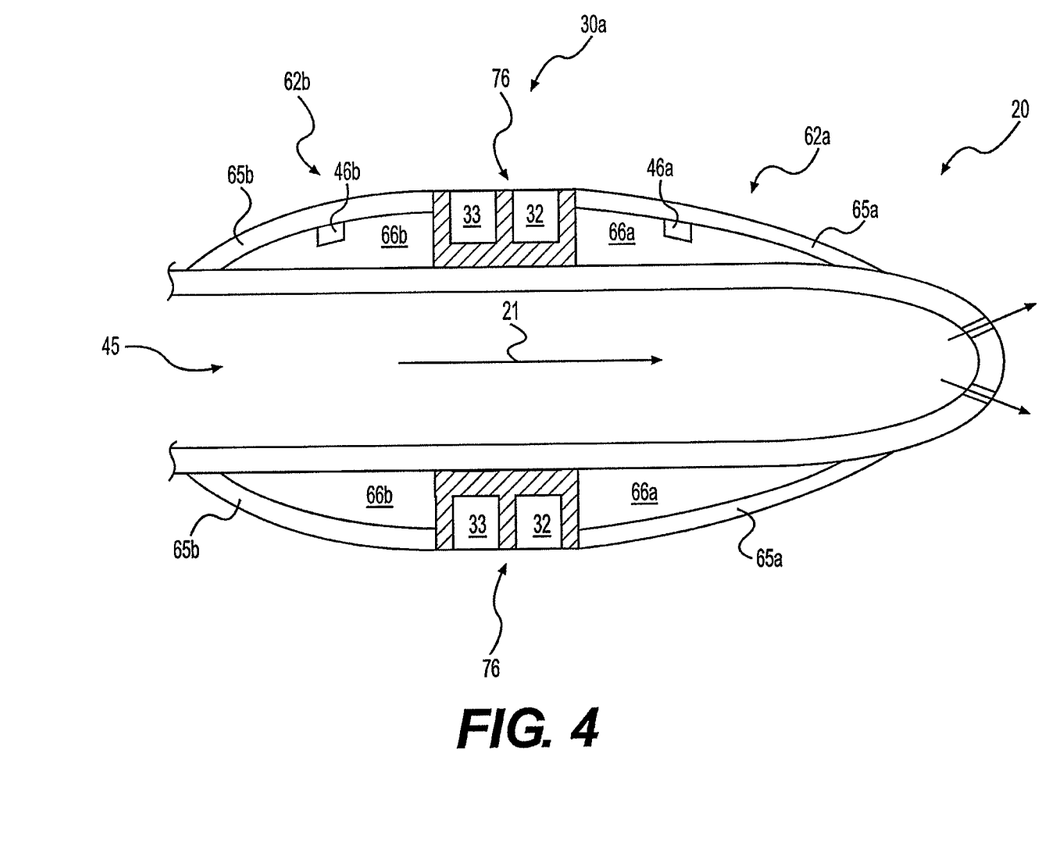
FIG. 4 illustrates a cross-sectional view of another embodiment of an ablation electrode.

In some embodiments, electrode 20 could include two or more insulating chambers. FIG. 4 illustrates one embodiment of electrode 20 having a first insulating chamber 62a and a second insulating chamber 62b. As described above, insulating chambers 62a, 62b may include one or more side walls 65a, 65b that may generally extend at least partially about electrode 20. As previously described, insulating chambers 62a, 62b can be variously shaped and sized. Also, insulating chambers 62a, 62b can include volumes 66a, 66b that may be filled with various or different insulating materials. Chambers 62a, 62b could be differently configured, and may include multiple temperature sensors 46a, 46b.

FIG. 4 illustrates an embodiment of electrode 20 having one or more ring electrodes 30a. Specifically, ring electrodes 30a includes a distal ring electrode 32 and a proximal ring electrode 33. Other embodiments of electrode 20 could include more or less ring electrodes 30a configured to sense a physiological signal.

In some embodiments, ring electrodes 30a could extend at least partially about electrode 20. Also, ring electrodes 32, 33 may be separated by an insulating material 76. Insulating material 76 could separate one or more ring electrodes from each other, one or more insulating chambers 62a, 62b, or electrode 20. Insulating material 76 may be different to insulating material contained with volumes 66a, 66b. In some embodiments, the insulating materials could be similar.

Figure 5:
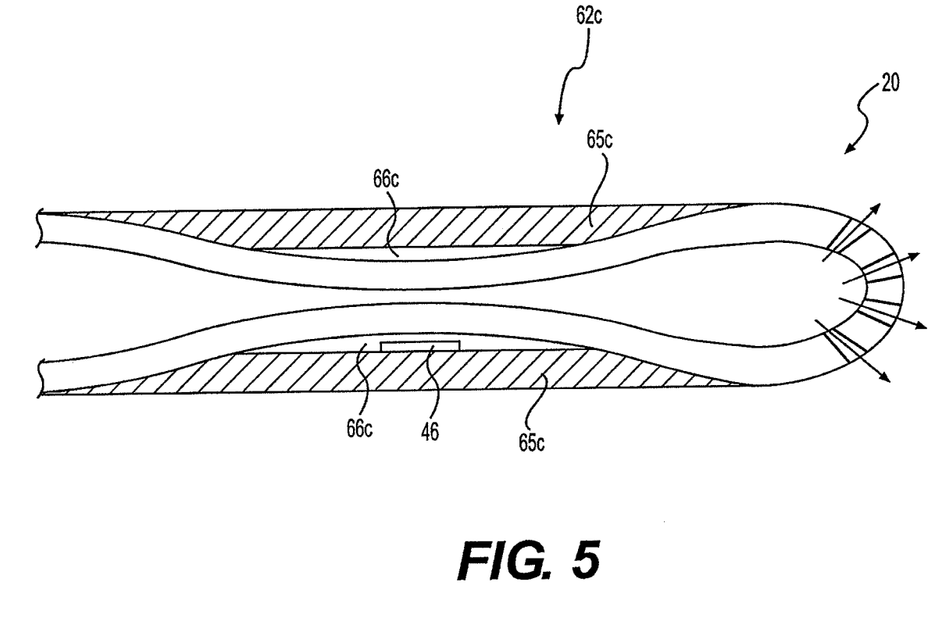
FIG. 5 illustrates a cross-sectional view of another embodiment of an ablation electrode.

FIG. 5 illustrates another embodiment of electrode 20. As shown, electrode 20 and insulating chamber 62c can be configured to form an outer structure having a substantially similar cross-section along its longitudinal axis. Specifically, electrode 20 can include a concave region configured to provide a concave sidewall of volume 66c. Another sidewall of volume 66c can be provided by a generally linear sidewall 65c, such that insulating chamber 62c can have an outer diameter similar to the outer diameter of electrode 20 at its distal end.

As illustrated in FIGS. 2, 4 and 5, temperature sensor 46 can be positioned within insulating chamber 62. Electrically conductive wires can extend through elongate body 12 or electrode 20 to deliver energy or to permit communication with sensor 46. In other embodiments, sensor 46 can be positioned about insulating chamber 62. In one aspect, the limited thermal conductivity of insulating chamber 62 facilitates accurate temperature sensing of the region surrounding electrode 20. For example, insulating chamber 62 can provide sufficient thermal insulation such that a temperature of the surrounding region is approximately equal to the temperature of sidewall 65 or insulating chamber 62.

Figure 6A:
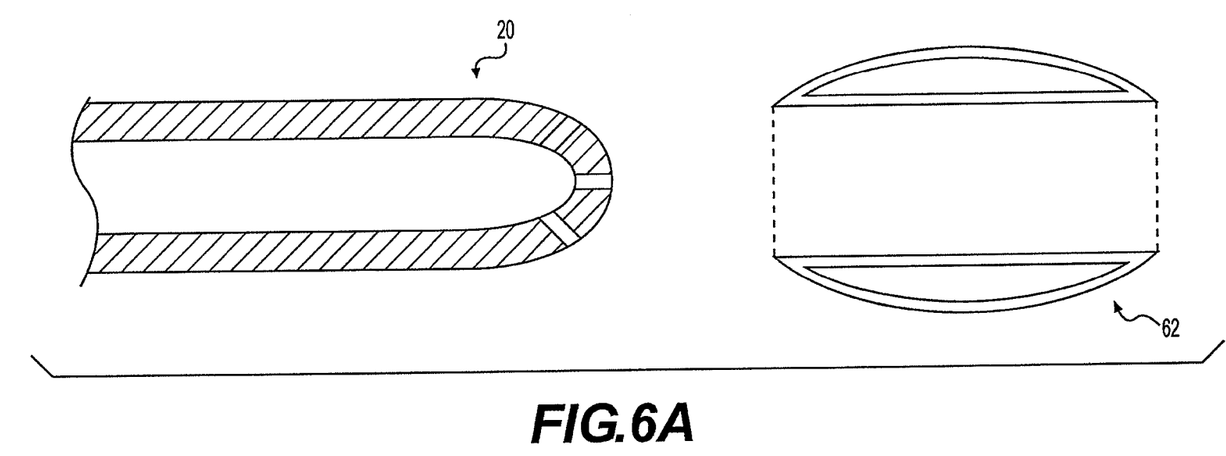
FIG. 6A illustrates a method of manufacturing an ablation electrode as described herein.
Figure 6B:
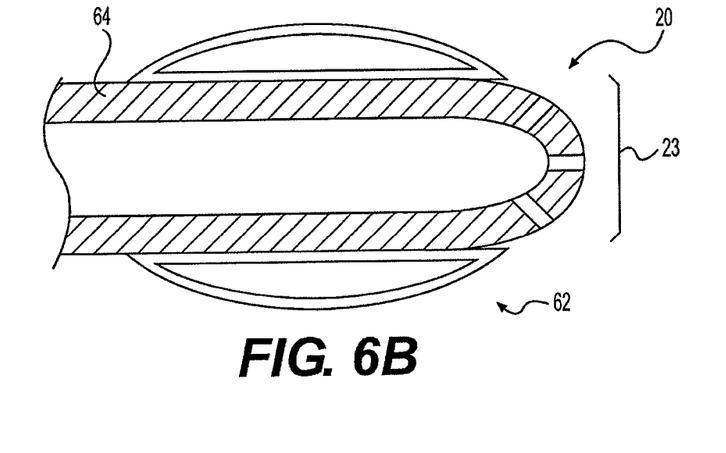
FIG. 6B illustrates a method of manufacturing an ablation electrode.

Various methods may be used to manufacture ablation electrode 20 or insulating chamber 62. For example, as shown in FIG. 6A, both electrode 20 and insulating chamber 62 can be preformed as two separate components. All or a portion of insulating chamber 62 can be defined by a separate structure and can be configured to mate with part of electrode 20. As illustrated in FIG. 6B, both components may then be combined to form a complete electrode assembly. Alternatively, as shown in FIGS. 2 to 5, one or more sidewalls 65 may be attached to sidewalls 64 to form insulating chambers 62. Such attachment can include welding, soldering, gluing, or other suitable methods.

The concept of an electrode and an insulating chamber may be discussed as separate elements for the sake of convenience or clarity, but such a description does not limit electrode 20, as described or claimed, to a configuration in which the insulating chamber 62 is a distinct structure mated with electrode 20. In addition, the outer surface of insulating chamber 62 can define a portion of the outer surface of electrode 20. For example, sidewall 65 can define the outer surface of electrode 20. Also, part of insulating chamber 62 could be manufactured from material similar or different to a material used to manufacture electrode 20. For example, sidewall 65 could be similar or different material to sidewall 64.

Irrigation apertures 23 can be formed in a variety of ways. In one aspect, channels can be drilled through sidewall 64. While a macroporous electrode 20 is illustrated in the figures, microporous structures are also contemplated. For example, the sidewall 64 could be formed from sintered material having a porosity which allows cooling fluid flow therethrough. One skilled in the art will appreciate that a variety of conventional macro or microporous catheter materials can be utilized to form electrode 20.

One skilled in the art will appreciate that the shape of electrode 20 can be varied according to the use of device 10. For example, another embodiment of ablation electrode 20 could include a blunt distal end. Other embodiments of the present disclosure will be apparent to those skilled in the art from consideration and practice of the specification. It is intended that the specification and examples be considered as exemplary only, with a true scope and spirit of the present disclosure being indicated by the following claims.

The invention claimed is:

1. A catheter device configured for vascular access, comprising:
    an elongate body extending between a proximal end and a distal end, wherein the elongate body includes a lumen configured to receive a fluid;
    an ablation electrode configured to provide ablative energy, wherein the ablation electrode is located distally along the elongate body and includes an inner surface, the inner surface defining a passageway fluidly connected to the lumen of the elongate body, wherein the ablation electrode includes a plurality of irrigation apertures fluidly connected to the lumen;
    a sensor configured to provide a signal representative of temperature; and
    an insulating chamber extending at least partially about an outer surface of the ablation electrode, wherein the outer surface has a diameter greater than a diameter of the inner surface, wherein the insulating chamber is configured to at least partially insulate the sensor from the ablation electrode, wherein the irrigation apertures are outside of the insulating chamber.

2. The device of claim 1, wherein the insulating chamber extends substantially about an outer surface of the ablation electrode.

3. The device of claim 1, wherein the insulating chamber includes at least one of a fluid and a solid material.

4. The device of claim 3, wherein the fluid includes at least one of air, nitrogen, water, and a saline solution.

5. The device of claim 3, wherein the solid material includes at least one of a foam, a polymer, and a ceramic material.

6. The device of claim 1, wherein the sensor is located within the insulating chamber.

7. The device of claim 1, further including at least one ring electrode located proximal to a distal end of the ablation electrode and along the elongate body.

8. The device of claim 7, further including a second insulating chamber located proximal to at least one of the at least one ring electrodes.

9. The device of claim 1, further including a ring electrode at least partially located about the insulating chamber.

10. The device of claim 1, further including an articulation section located distally along the elongate body and controlled by a control mechanism.

11. An ablation electrode device configured to provide ablative energy to cardiac tissue, comprising:
    an ablation electrode having:
        a proximal section configured for attachment to an elongate body of a catheter device;
        an inner surface defining a passageway configured to connect to a lumen of the elongate body, wherein the passageway is configured to receive a fluid;
        a plurality of irrigation apertures fluidly connected to the passageway;
        a sensor configured to provide a signal representative of a temperature of a region external to the ablation electrode; and
        an insulating chamber extending at least partially about an outer surface of the ablation electrode, wherein the outer surface has a diameter greater than a diameter of the inner surface, wherein the insulating chamber is configured to at least partially insulate the sensor, wherein the sensor is disposed within the insulating chamber and is spaced apart from the ablation electrode, wherein the irrigation apertures are outside of the insulating chamber.

12. The electrode device of claim 11, wherein the insulating chamber extends substantially about the outer surface of the ablation electrode.

13. The electrode device of claim 11, wherein the insulating chamber includes at least one of a fluid and a solid material, wherein the fluid includes at least one of air, nitrogen, water, and a saline solution, and the solid material includes at least one of a foam, a polymer, and a ceramic material.

14. The electrode device of claim 11, wherein the sensor is located within the insulating chamber.

15. The electrode device of claim 11, wherein the ablation electrode is substantially linear and generally cylindrical.

16. The electrode device of claim 11, wherein the ablation electrode is rigid.

17. The electrode device of claim 11, further including at least one ring electrode located proximal to a distal end of the ablation electrode and along the ablation electrode.

18. The electrode device of claim 17, further including a second insulating chamber located proximal to at least one of the at least one ring electrodes.

19. A method of manufacturing an ablation electrode, comprising the steps of:
provide a wall having an inner surface defining a passageway configured to connect to a lumen of an elongate body of a catheter device, wherein the passageway is configured to receive a fluid;
forming a plurality of irrigation apertures in the wall such that the irrigation apertures are fluidly connected to the passageway;
providing an insulating chamber extending at least partially about an outer surface of the ablation electrode, wherein the outer surface has a diameter greater than a diameter of the inner surface, wherein the irrigation apertures are outside of the insulating chamber; and
placing a sensor within the insulating chamber, wherein the sensor is configured to provide a signal representative of a temperature of a region external to the ablation electrode.

20. The method of claim 19, wherein providing an insulating chamber includes sealing the insulating chamber prior to forming the ablation electrode.

21. The method of claim 19, wherein the insulating chamber is filled with at least one of a fluid and a solid material, wherein the fluid includes at least one of air, nitrogen, water, and a saline solution, and the solid material includes at least one of a foam, a polymer, and a ceramic material.

22. The method of claim 19, wherein the insulating chamber is formed from at least one of an alloy, a polymer, and a ceramic material.

* * * * *